(12) United States Patent
Schmieding

(10) Patent No.: US 7,862,567 B2
(45) Date of Patent: Jan. 4, 2011

(54) RETRODRILL TECHNIQUE FOR INSERTION OF AUTOGRAFT, ALLOGRAFT OR SYNTHETIC OSTEOCHONDRAL IMPLANTS

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1078 days.

(21) Appl. No.: 11/602,978

(22) Filed: Nov. 22, 2006

(65) Prior Publication Data

US 2007/0093842 A1 Apr. 26, 2007

Related U.S. Application Data

(62) Division of application No. 10/792,780, filed on Mar. 5, 2004, now Pat. No. 7,160,305.

(60) Provisional application No. 60/452,527, filed on Mar. 7, 2003.

(51) Int. Cl.
*A61B 17/16* (2006.01)

(52) U.S. Cl. ....................................................... 606/80

(58) Field of Classification Search ............... 606/79, 606/80, 84, 85, 82, 87, 88, 96, 102, 104, 606/300, 301, 304, 311, 315, 318; 408/24, 408/36, 227
See application file for complete search history.

(56) References Cited

U.S. PATENT DOCUMENTS

| | | | |
|---|---|---|---|
| 4,034,418 A | 7/1977 | Jackson et al. | |
| 4,341,206 A * | 7/1982 | Perrett et al. | ............ 606/80 |
| 5,211,647 A | 5/1993 | Schmieding | |
| 5,374,270 A | 12/1994 | McGuire et al. | |
| 5,435,672 A * | 7/1995 | Hall et al. | ............ 408/68 |
| 5,919,196 A | 7/1999 | Bobic et al. | |
| 6,015,411 A | 1/2000 | Ohkoshi et al. | |
| 6,132,433 A | 10/2000 | Whelan | |
| 6,149,654 A | 11/2000 | Johnson | |
| 6,280,474 B1 | 8/2001 | Cassidy et al. | |

OTHER PUBLICATIONS

Y. Ohkoshi, et al., "Description of a New Endoscopic Posterior Cruciate Ligament Reconstruction and Comparison with a 2-Incision Technique", *Arthroscopy: The Journal of Arthroscopic and Related Surgery*, vol. 19, No. 8, Oct. 2003, pp. 825-832.

Y. Ohkoshi, et al., "A New Endoscopic Posterior Cruciate Ligament Reconstruction: Minimization of Graft Angulation", *Arthroscopy: The Journal of Arthroscopic and Related Surgery*, vol. 17, No. 3, Mar. 2001, pp. 258-263.

* cited by examiner

*Primary Examiner*—Eduardo C Robert
*Assistant Examiner*—David Comstock
(74) *Attorney, Agent, or Firm*—Dickstein Shapiro LLP

(57) ABSTRACT

Osteochondral sockets are formed using a retrograde drill assembly. The retrograde drill assembly includes a guide pin having a fluted tip and an externally threaded portion. A removable cutter head has internal threads that engage the threads of the guide pin. The guide pin is drilled through bone, exposing the external threads in a joint space requiring repair. The cutter is threaded onto the guide pin, and the assembly is retrograded with rotation to form a socket in the bone. The cutter is disengaged from the guide pin for disassembly and removal from the bone, making way for an implant to be installed in the pocket. The implant can be drawn into the socket using an attached strand threaded through the bone socket and out of the bone.

7 Claims, 9 Drawing Sheets

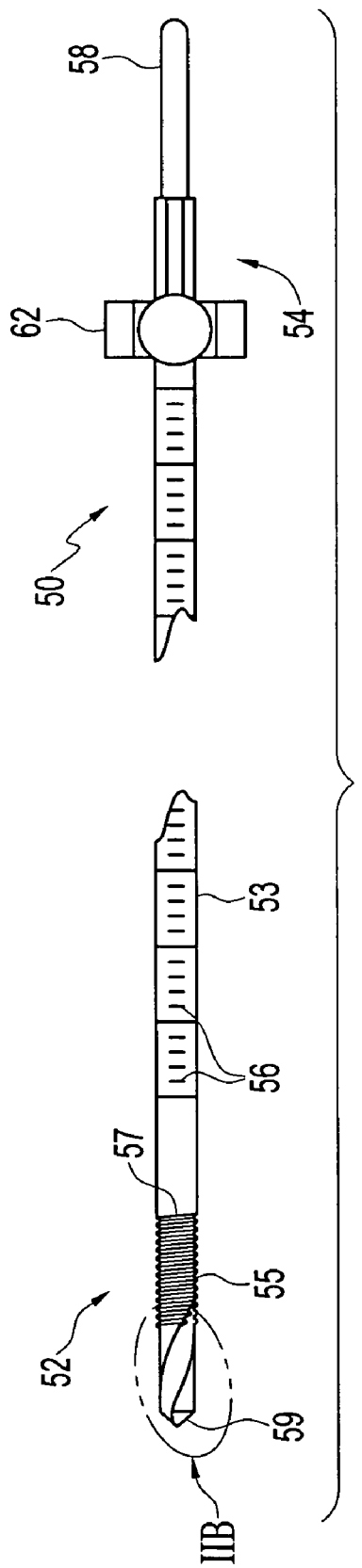
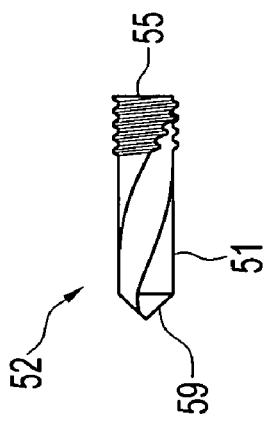
FIG. 2A
FIG. 2B

RETRODRILL TECHNIQUE FOR INSERTION OF AUTOGRAFT, ALLOGRAFT OR SYNTHETIC OSTEOCHONDRAL IMPLANTS

RELATED APPLICATIONS

This application is a divisional of application Ser. No. 10/792,780, filed Mar. 5, 2004 now U.S. Pat. No. 7,160,305, which claims the benefit of U.S. provisional application No. 60/452,527, filed Mar. 7, 2003, the disclosure of which is incorporated herein by reference.

FIELD OF THE INVENTION

The present invention relates to the field of surgery and, more particularly, to methods and apparatus for retrograde repair of osteochondral defects.

BACKGROUND OF THE INVENTION

Methods and apparatus related to arthroscopic osteochondral transplantation for repairing chondral defects are known in the art. For example, U.S. Pat. No. 5,919,196, the disclosure of which is incorporated by reference herein, involves autograft transplantation using matched graft harvesters and recipient site harvesters, in the form of tubes with collared pins, to create and transplant donor graft osteochondral cores into correspondingly sized recipient sockets.

Although the above-described procedure is a significant improvement over prior art techniques for osteochondral transplantation, it is difficult to access defects on the tibial plateau using donor and recipient harvesters, as required in the technique of the '196 patent.

Accordingly, it would be desirable to provide apparatus and methods for creating the recipient site socket from the inside out, i.e., using a retrograde technique. It would also be desirable to provide a technique for inserting the replacement osteochondral core or implant in a retrograde manner to obviate inserting a harvester into the joint.

SUMMARY OF THE INVENTION

The present invention overcomes the disadvantages of the prior art and fulfills the needs noted above by providing a retrograde osteochondral system by which a grafted healthy bone or synthetic implant is implanted into the recipient site in a retrograde manner.

The retrograde osteochondral system of the present invention employs a retrodrill device for osteochondral reconstruction. The retrodrill device is provided with a retrograde cutter that is detachable from a guide pin. The cutter has a cannulated body provided with a plurality of cutting flutes on a proximal face and disposed radially. The guide pin includes a cannulated body with a proximal end and a distal end, and a trocar disposed in the lumen of the cannulated body. The exterior of the cannulated body is provided with graduated depth markings. The cannulated body of the guide pin has threads toward the distal end for receiving corresponding threads in the cannulation of the retrodrill cutter.

According to one embodiment of the present invention, retrograde osteochondral reconstruction is conducted using the retrodrill cutter in a retrograde manner to form a recipient socket at the location of an osteochondral lesion developed on the head of the tibia, for example. Socket depth is gauged using by employing depth markings on the cannulated retrodrill guide pin. More specifically, formation of the recipient socket begins by using the retrodrill guide pin with the inserted trocar to drill a tunnel through an upper portion of the tibia, from behind and through the osteochondral lesion, and into the tibial joint space. A drill guide with a marking hook placed on the lesion is used to ensure accurate placement of the guide pin. The retrodrill cutter is then inserted into the joint space and oriented perpendicularly to the tibial lesion so that the guide pin can be inserted into, and threadingly engaged with, the retrodrill cutter. Once secured to the retrodrill cutter, the guide pin is retracted until the proximal cutting face of the retrodrill cutter contacts the tibial osteochondral lesion. The retrodrill cutter is then rotated and further retracted through the osteochondral lesion and into the tibia to the proper depth as measured on the outside of the knee by the depth markings on the guide pin. The retrodrill cutter is advanced out of the completed socket, and disengaged from the retrodrill guide pin by applying a reverse drilling motion to the guide pin while holding the cutter stationary.

A core, such as a graft bone core or a synthetic implant, is fitted with a length of suture to provide a means for pulling the core into the tibial recipient socket described above. The length of suture preferably passes through a longitudinal cannulation in the core, made available by removing the trocar, and is secured to the core using either a knot at the back end, an adhesive, insert molding, or equivalent securing methods. The suture extends through the leading tip of the core a sufficient length to allow the suture to pass through the cannulated retrodrill guide pin and be grasped for pulling the core into the tibial socket.

Other features and advantages of the present invention will become apparent from the following description of the invention, which refers to the accompanying drawings.

BRIEF DESCRIPTION OF THE DRAWINGS

FIGS. 2A-2B illustrate a retrodrill guide pin including a cannulated body and a trocar according to the present invention.

DETAILED DESCRIPTION OF THE PREFERRED EMBODIMENT

The present invention provides a retrodrill technique and apparatus for providing a recipient bone site or socket that is formed in a retrograde manner during retrograde osteochondral repair. A core, such as a grafted healthy bone or a synthetic implant, is installed into the recipient bone socket in a retrograde manner.

Figure 1C:
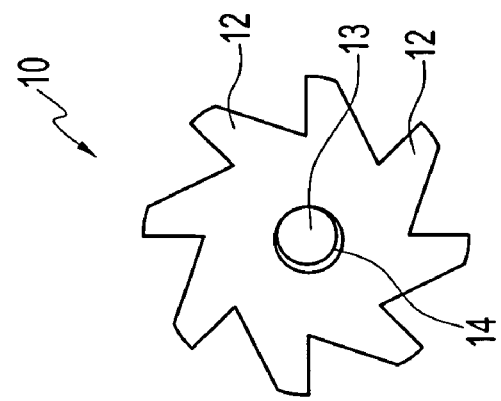
FIGS. 1A-1C illustrate a retrodrill cutter according to the present invention.
Figure 1B:
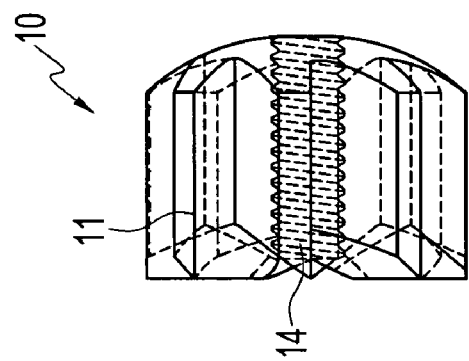
Figure 1A:
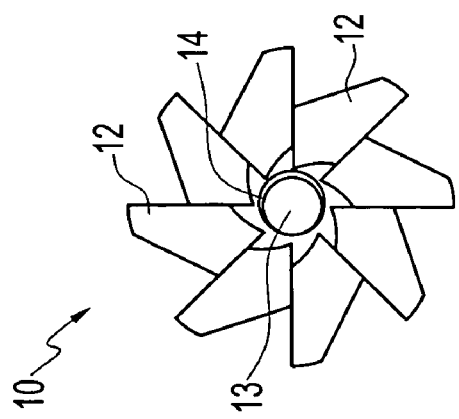

Referring now to the drawings, where like elements are designated by like reference numerals, FIGS. 1-2 illustrate a retrodrill cutter 10 (FIGS. 1A-1C) which is adapted to be threadedly engaged by a retrodrill guide pin 50 (FIGS. 2A and 2B). The retrodrill cutter 10 is formed of a cannulated body 11 surrounded by a plurality of cutting flutes formed by longitudinal teeth 12. Cannulation 13 has internal threads 14, discussed further below.

The retrodrill guide pin 50 has a proximal end 54, a distal end 52, and a cannulated body 53, which is lazed with calibrated depth markings 56. The lumen of the cannulated body accepts a trocar 58 having a pointed tip 59. When the trocar is removed, a strand of suture can be passed through the lumen of the cannulated body. The proximal end 54 of the cannulated body of retrodrill guide pin 50 is configured for chucking into a rotary driver (not shown) and includes a setscrew collar 62 for securing an axial position of the trocar 58 in the cannulated body 53. The distal end 52 of the retrodrill guide pin 50 is open at the tip to expose the pointed end 59 of the trocar 58. Distal end 52 also features a fluted region 51 and a threaded region 55 (FIG. 2B). Threaded region 55 is designed to engage corresponding threads 14 provided in the cannulation 13 of the retrodrill cutter 10. Accordingly, the diameter of the cannula 13 of the retrodrill cutter 10 closely approximates the diameter of outer threaded region 55 of the retrodrill guide pin 50, to allow engagement of the outer threaded region 55 with the inner threads 14 of retrodrill cutter 10.

The threaded region 55 has an outer diameter that closely approximates, and preferably is less than, the diameter of shaft 53. Threaded region 55 terminates proximally to meet a shoulder 57 established by the remaining portion of shaft 53, the shoulder 57 providing a stop for the inner threads of cutter 10. Threaded region 55 and fluted tip 51 partially overlap. A portion of the fluted tip extends distally beyond threaded region 55, preferably substantially the length of the threaded cannula of the cutter. Accordingly, the cutter can be positioned conveniently over an unthreaded portion of the fluted tip as an initial step of assembling the cutter onto the guide pin.

A preferred method of forming a tibial socket using the retrodrill guide pin 50 and the retrodrill cutter 10 of the present invention, and then installing core 46 within the formed tibial socket, is described below with reference to FIGS. 3-9.

Figure 3:
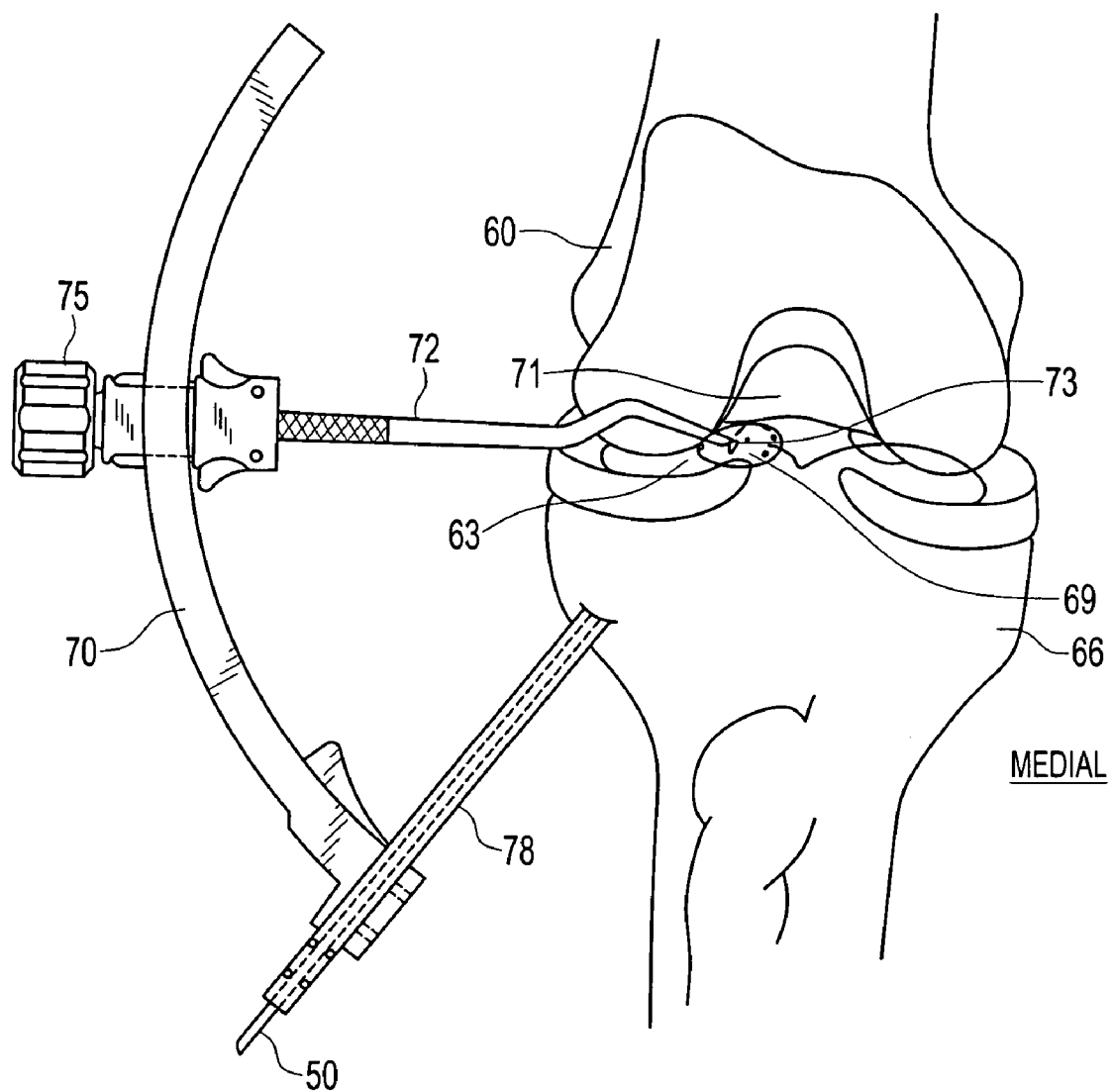
FIG. 3 schematically illustrates the formation of a socket at a tibial recipient site according to the present invention.

FIG. 3 illustrates a schematic anterior view of a knee 60 in which osteochondral lesion or defect 69 is located on tibial plateau 63 of tibia 66. Standard diagnostic arthroscopy is employed to evaluate the location and extent of the osteochondral lesion 69, as well as the defect pathology. As described below, the osteochondral lesion 69 is drilled out by employing a retrodrill technique in connection with a retrograde osteochondral repair method of the present invention.

A long adapter drill guide 70, for example an Arthrex C-Ring cross-pin drill guide such as those disclosed in U.S. Pat. Nos. 5,350,383 and 5,918,604, the disclosures of which are incorporated by reference herein, is secured to the lateral thigh, as shown in FIG. 3. Marking hook 72 of the adapter drill guide 70 is inserted into the joint space near intercondylar notch 71 and positioned over the osteochondral lesion 69 of the tibial plateau 63. Hook 72 includes a laser mark located anterior to tip 73 of the marking hook 72, to ensure placement of a guide pin 50 at a ninety-degree retrograde entry relative to the osteochondral lesion 69. The marking hook is held in position on the drill guide 70 by tightening knurled knob 75.

Once the drill guide 70 is properly positioned, cannulated retrodrill guide pin 50 is placed through sleeve 78 of the drill guide 70. Referring to FIG. 2A, trocar 58 is inserted in the cannulation of guide pin 50 and secured in place using setscrew collar 62 to provide the guide pin 50 with a pointed tip.

Figure 4:
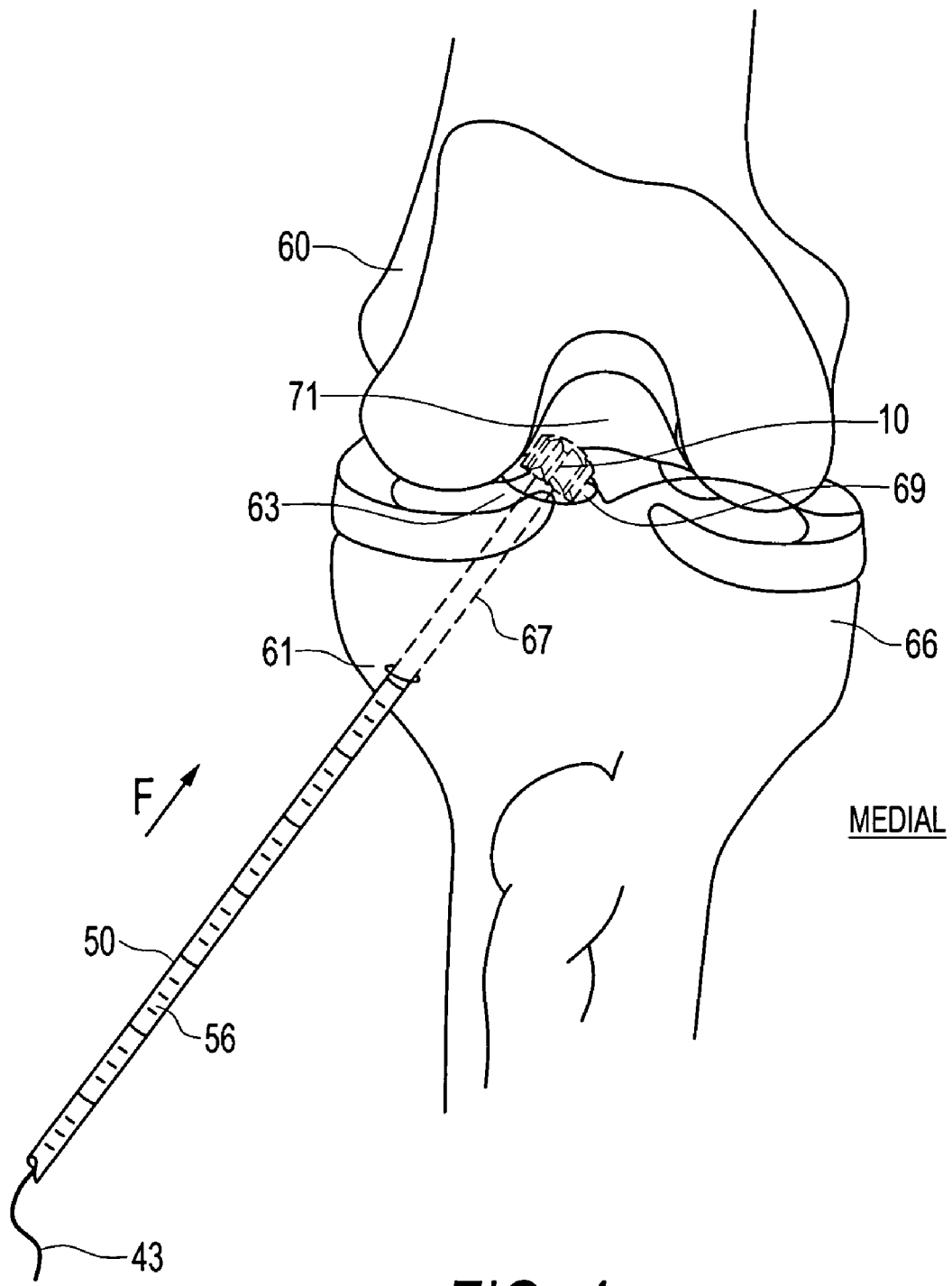
FIG. 4 schematically illustrates the formation of a tibial recipient socket at a stage subsequent to that shown in FIG. 3.
Figure 5:
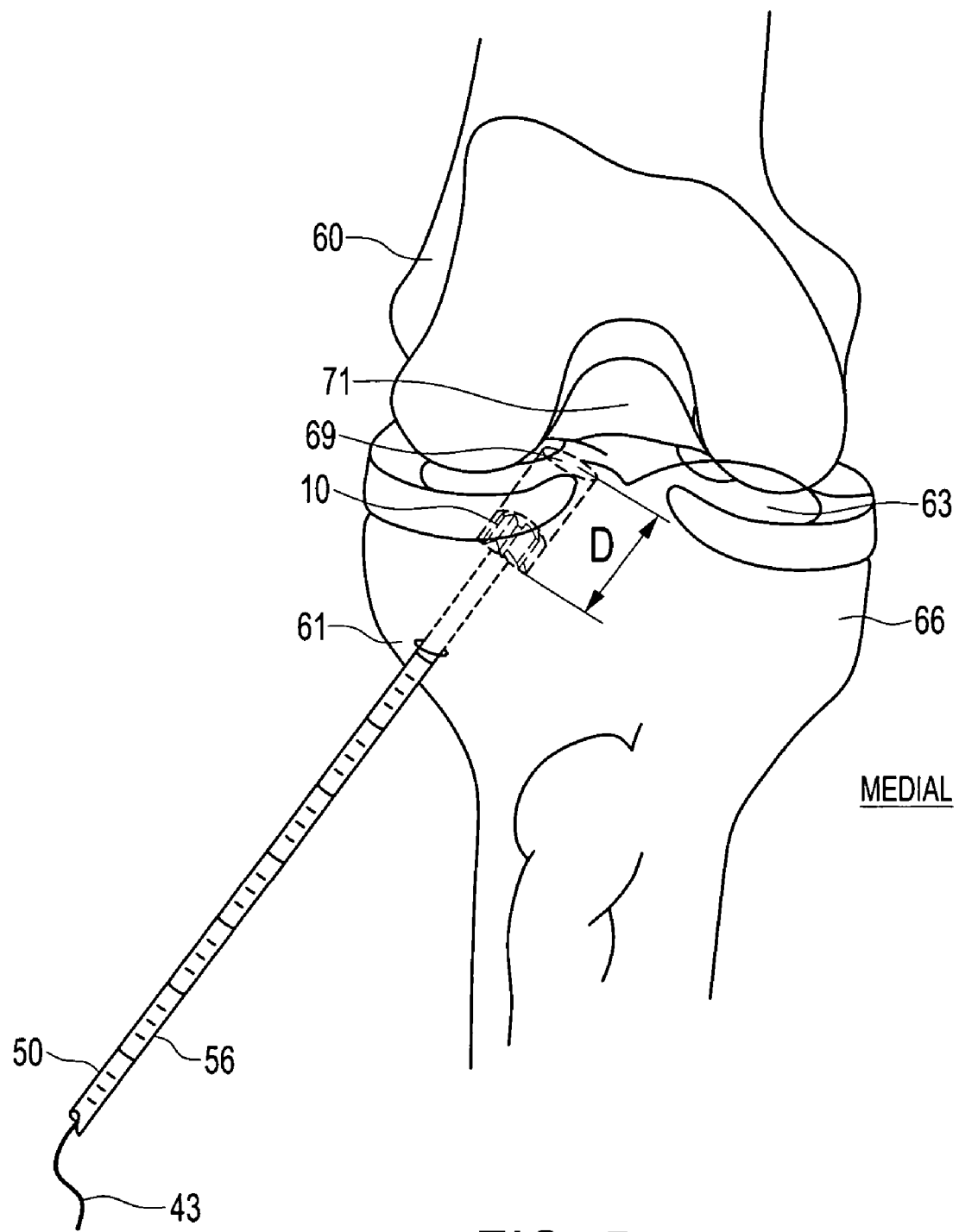
FIG. 5 schematically illustrates the formation of a tibial recipient socket at a stage subsequent to that shown in FIG. 4.
Figure 6:
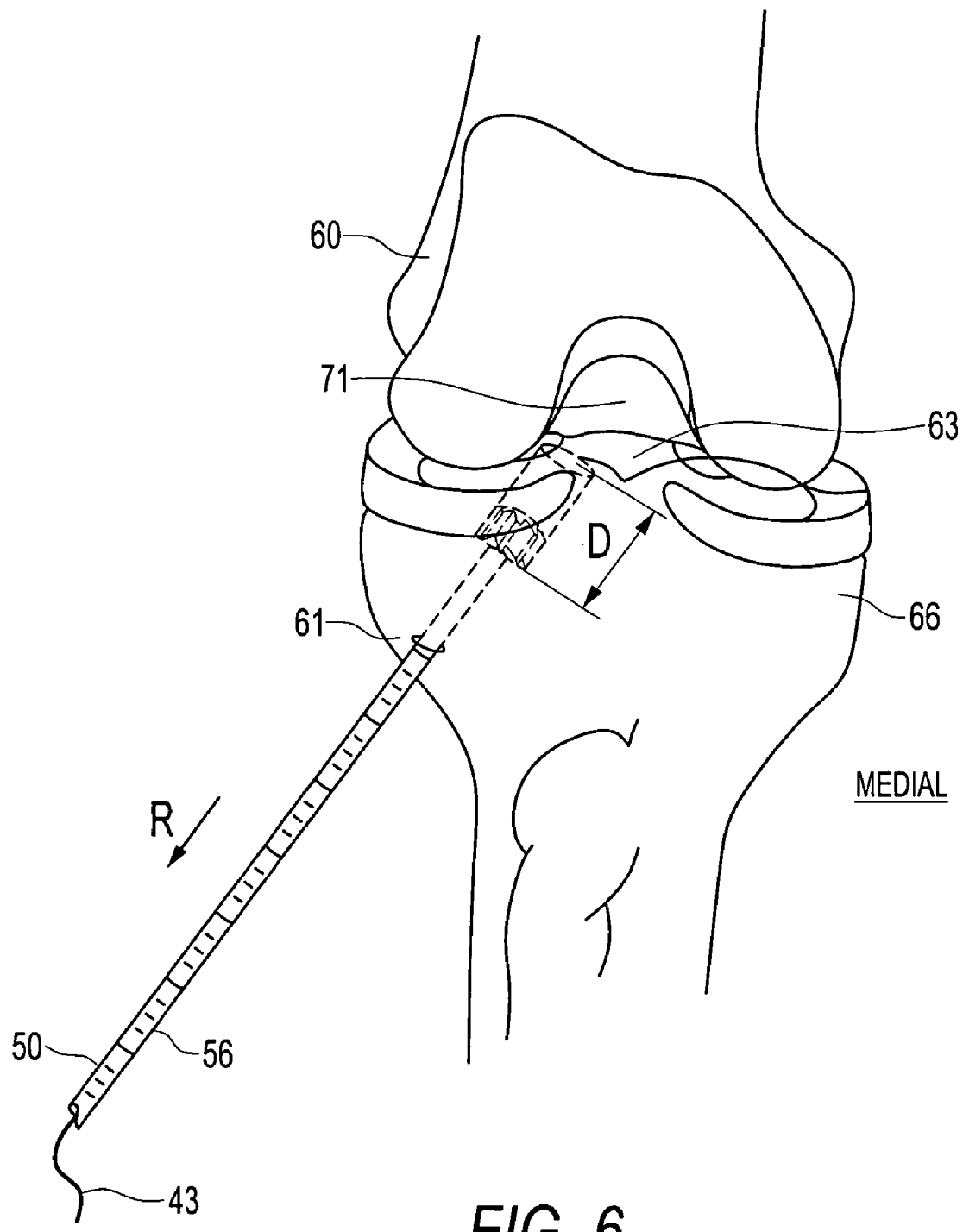
FIG. 6 schematically illustrates the formation of a tibial recipient socket at a stage subsequent to that shown in FIG. 5.

As shown in FIG. 4, the guide pin 50 is installed through the bone in an anterior-to-posterior direction relative to the osteochondral lesion 69, forming a narrow (3 mm) tunnel 67 through the bone and perpendicular to the osteochondral lesion 69. The cannulated retrodrill guide pin 50 is drilled through the lesion toward the tibial joint space until contact is made with the marking hook 72 of long adapter drill guide 70.

Once the guide pin is drilled into the tibial space, the trocar 58 is removed, and a strand 43 is inserted in its place through the cannulated body and into the joint space. An end of the strand is placed through the cannulation of retrodrill cutter 10 and secured, and the retrodrill cutter 10 is drawn into the joint space and aligned perpendicularly with the tibial lesion 69 and the guide pin 50. The threaded retrodrill guide pin 50 is inserted and engaged with the threads of the cannulated retrodrill cutter 10 by rotating and advancing the guide pin 50 in the direction of arrow F (FIG. 4) with respect to the retrodrill cutter 10. Optionally, placement of retrodrill cutter 10 employs a grasper or a similar device (not shown), for example.

Once engaged within the retrodrill cutter 10, the cannulated retrodrill guide pin 50 is chucked into a rotary driver and retracted until the proximal face of retrodrill cutter 10 contacts the tibial plateau 63 and lesion 69. At this point, a first reading of the markings 56 on the cannulated retrodrill guide pin 50 is recorded relative to anterior tibial skin surface 61.

Figure 7:
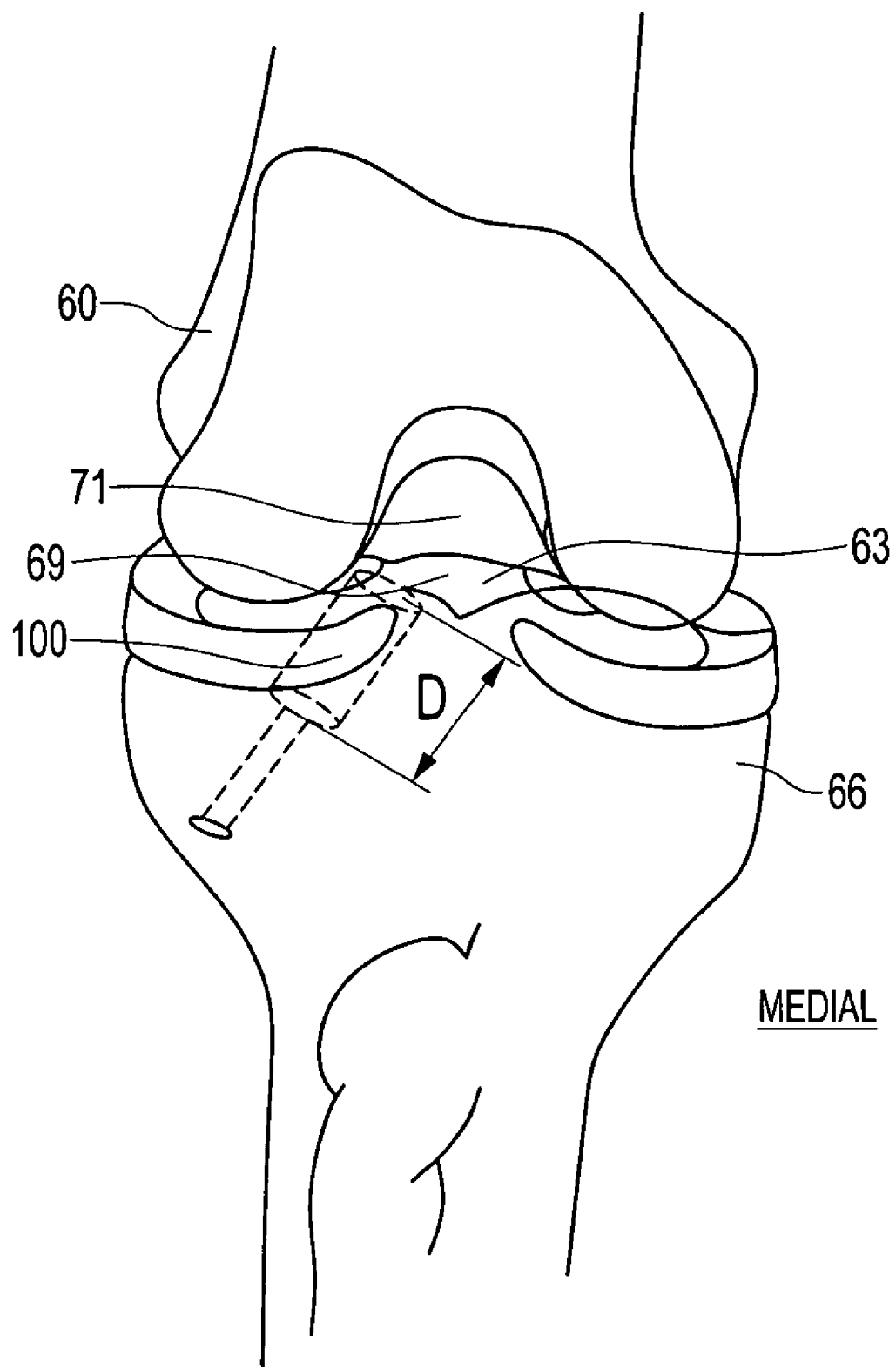
FIG. 7 schematically illustrates a completed socket formed at the tibial recipient site.

The cannulated retrodrill guide pin 50 is then rotated and retracted so that the proximal cutting face of retrodrill cutter 10 cuts through the surface of osteochondral lesion 69 and into the underlying bone, thereby forming a tibial recipient socket 100 as shown schematically in FIG. 7, in which representations of the surgical apparatus having been omitted for clarity. A second reading of the markings 56 on the retrodrill guide pin 50, recorded relative to the anterior tibial skin surface 61, is used to gauge the depth D of the retrodrill cutter 10 into the tibia 66. For example, once the first reading of the markings has been recorded, the surgeon could count about thirty markings 56 to the second reading, which would correspond to a depth D of about 5 to about 10 millimeters depending upon the mark spacing.

After drilling the retrodrill cutter 10 into the tibia 66 and completing the socket, the retrodrill guide pin remains in place, and is advanced to urge cutter 10 out of the socket. The retrodrill cutter 10 is disengaged from the retrodrill guide pin 50 by a reverse drilling motion, in the direction of arrow R of FIG. 6. The retrodrill cutter 10 is disengaged from the end of stand 43, by cutting the strand, for example. The end of strand 43 is secured to remain in place and available in the joint space by tying a knot, for example, to prevent the strand from being pulled back through cannulated body 53.

Figure 8:
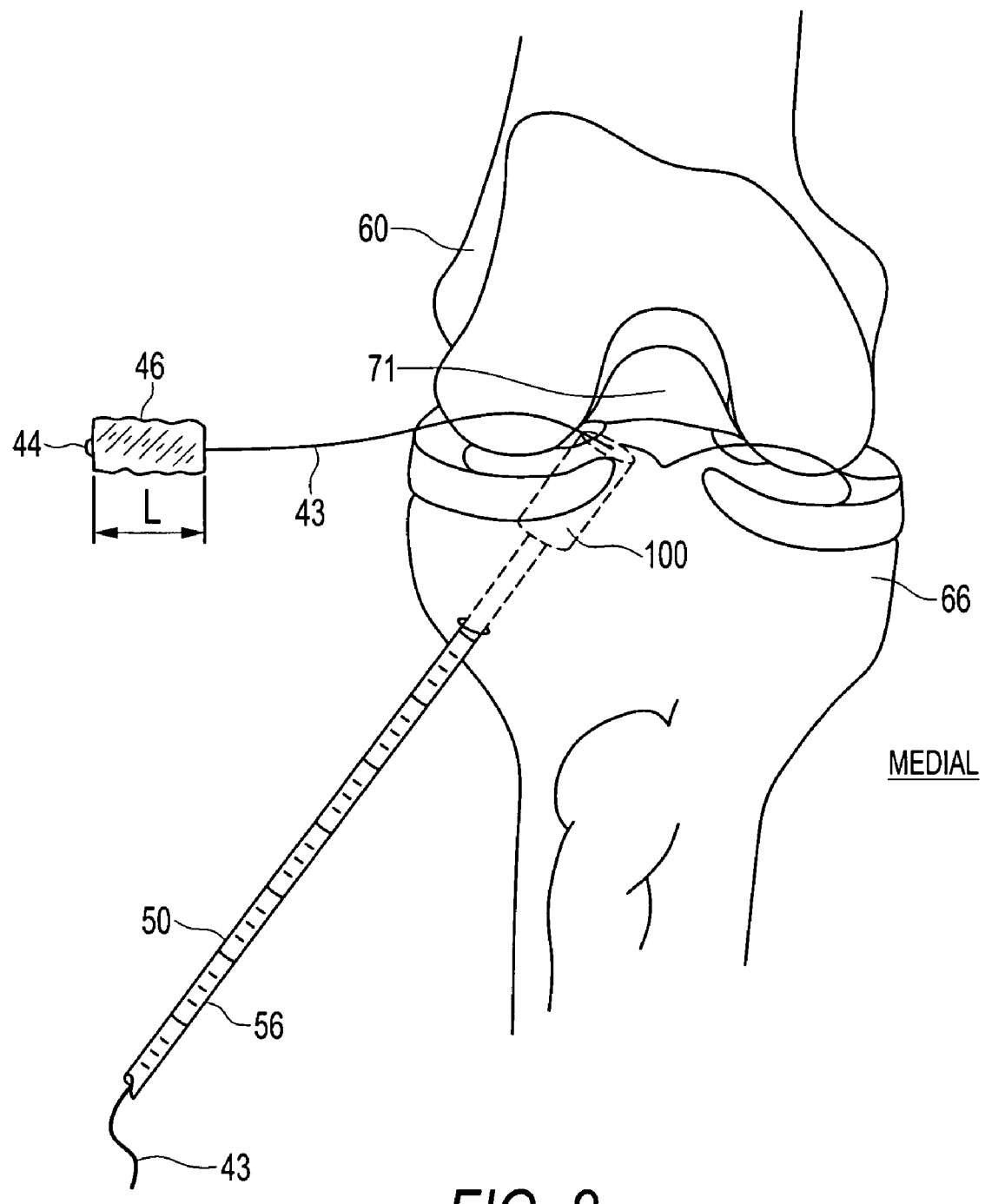
FIG. 8 schematically illustrates the installation of an osteochondral core within the tibial socket formed according to the present invention.
Figure 9:
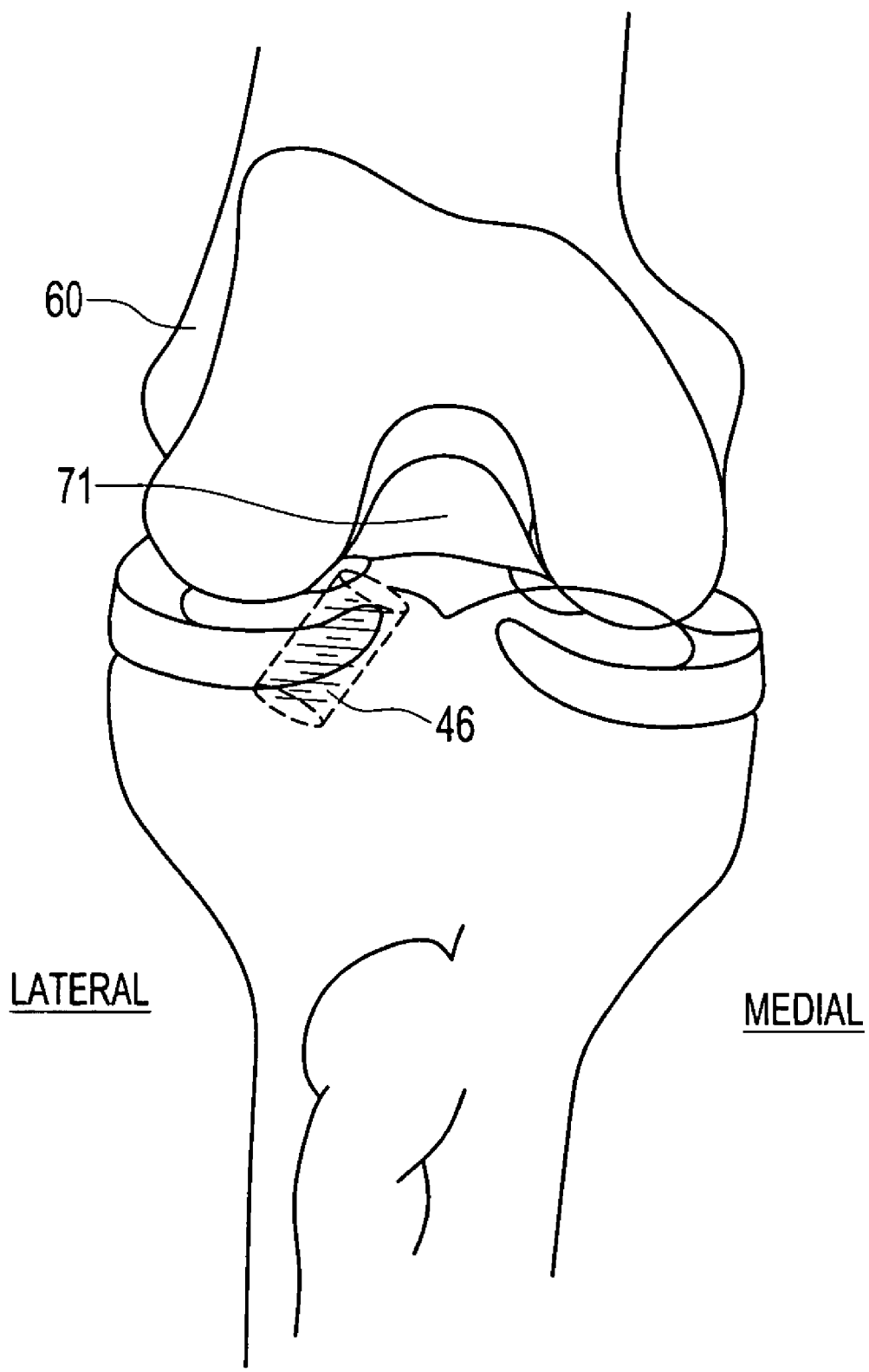
FIG. 9 schematically illustrates the installation of osteochondral core at a stage of processing subsequent to that shown in FIG. 8.

Reference is now made to FIG. 8, which shows the retrograde insertion of an osteochondral core or plug 46 into the recipient socket 100 of tibia 66. The core 46 is developed, for example, as a cannulated plug formed of a translucent or transparent polymer material, and preferably made of bioabsorbable materials such as polyglycolic or polylactic acid polymers. Optionally, core 46 is an autograft or autogenous bone core, or an allograft core, harvested by known methods of the art and subsequently employed in the retrograde osteochondral repair method of the present invention. Alternatively, the core 46 is a synthetic implant plug formed from a synthetic hydrogel, preferably Salubria™, having various shapes, preferably a cylindrical shape with one end being curved to match a portion of an articular surface. Salubria™ is a hydrogel composition, which is similar to human tissue in its mechanical and physical properties, and is sold by Salumedica of Atlanta, Ga.

Strand 43 is inserted through an opening formed through core 46, and is secured to the back end of the core by a ball or knot 44 (FIG. 8). If desired, the knot 44 is countersunk into the core 46 for permanent suture fixation. Alternatively, strand 43 is attached to core 46 by insert molding or adhesive.

The suture strand or wire 43 extending from the core 46 is passed outside the tibia, preferably through the lumen of cannulated body 53 of guide pin 50, the trocar 58 having been removed. Optionally, when using a non-cannulated guide pin, for example, strand 43 passes directly through the tunnel 67. The free end of strand 43 is captured outside the body and retracted to draw the suture or wire 43 through the guide pin 50. As the strand 43 is drawn, the core 46 is pulled into the joint space and pivoted into axial alignment with the tibial recipient socket 100. Continued tension on strand 43 draws core 46 into the tibial socket 100 in a retrograde fashion. One skilled in the art will realize that the amount of force for advancing the core 46 into the tibial recipient site 100 is directly proportional to the diameter and length (L) of the core 46, as well as the depth of the tibial socket 100.

Once the core 46 is secured within the tibial socket 100, the strand 43 exiting the lateral opening of the tibia can be secured with a button or a small diameter T-screw provided over or in the hole and substantially flush with the cortical bone. Alternatively, the strand 43 is removed, for example, by grasping the ball or knot 44 with a grasper or a similar device and drawing the strand out through the joint space. If complications occur, such as over-insertion of the core 46, the cannulated retrodrill guide pin 50 is employed to push the core out of the tibial site for corrections.

Although the present invention has been described in relation to particular embodiments thereof, many other variations and modifications and other uses will become apparent to those skilled in the art.

What is claimed is:

1. A retrograde drill comprising:
   a cutting head having a cylindrical body and a threaded cannulation extending through the cutting head, the cutting head being surrounded by a plurality of longitudinal cutting blades radiating symmetrically from the cylindrical body and having edges extending radially from the threaded cannulation; and
   a guide pin having a shaft with a proximal end and a distal end, and outer threads formed proximal to the distal end on the outside of the shaft and corresponding to inner threads of the threaded cannulation of the cutting head to allow assembling of the cutting head onto the outer threads of the guide pin, the distal end of the guide pin having a fluted drill tip for drilling bone.

2. A retrograde drill according to claim 1, wherein the fluted drill tip includes flutes that extend into the threads formed proximal to the distal end.

3. A retrograde drill according to claim 2, wherein the cannulation in the cutter has a length, and the fluted drill tip extends distally beyond the threads by the length of the threaded cannulation.

4. A retrograde drill according to claim 1, wherein the shaft of the guide pin is cannulated.

5. A retrograde drill according to claim 4, further comprising a trocar received in the cannulated guide pin shaft.

6. A retrograde drill according to claim 1, wherein the shaft has an outer diameter and the outer threads do not extend beyond the outer diameter of the shaft.

7. A retrograde drill according to claim 1, wherein the outer threads terminate proximally to form a stop for the inner threads of the cutting head.

* * * * *